（12) United States Patent
Krimsky

(10) Patent No.: US 10,448,886 B2
(45) Date of Patent: Oct. 22, 2019

(54) INDUCED ATELECTASIS AND PULMONARY CONSOLIDATION SYSTEMS AND METHODS

(71) Applicant: COVIDIEN LP, Mansfield, MA (US)

(72) Inventor: William S. Krimsky, Bel Air, MD (US)

(73) Assignee: COVIDIEN LP, Mansfield, MA (US)

( * ) Notice: Subject to any disclaimer, the term of this patent is extended or adjusted under 35 U.S.C. 154(b) by 419 days.

(21) Appl. No.: 15/238,939

(22) Filed: Aug. 17, 2016

(65) Prior Publication Data

US 2018/0049693 A1 Feb. 22, 2018

(51) Int. Cl.

| | | |
|---|---|---|
| *A61B 5/08* | (2006.01) | |
| *A61B 34/10* | (2016.01) | |
| *A61B 34/20* | (2016.01) | |
| *A61B 1/018* | (2006.01) | |
| *A61M 25/10* | (2013.01) | |
| *A61M 39/24* | (2006.01) | |
| *A61B 5/00* | (2006.01) | |
| *A61B 90/00* | (2016.01) | |
| *A61B 1/267* | (2006.01) | |
| *A61M 1/00* | (2006.01) | |
| *A61M 25/00* | (2006.01) | |
| *A61B 5/06* | (2006.01) | |

(52) U.S. Cl.
CPC ............ *A61B 5/4848* (2013.01); *A61B 1/018* (2013.01); *A61B 1/2676* (2013.01); *A61B 5/08* (2013.01); *A61B 5/4836* (2013.01); *A61B 34/10* (2016.02); *A61B 34/20* (2016.02); *A61B 90/37* (2016.02); *A61M 1/008* (2013.01); *A61M 25/0068* (2013.01); *A61M 25/10* (2013.01); *A61M 39/24* (2013.01); *A61B 5/062* (2013.01); *A61B 2034/107* (2016.02); *A61B 2034/2051* (2016.02)

(58) Field of Classification Search
CPC ....... A61B 5/4848; A61B 34/10; A61B 34/20; A61B 90/37; A61B 1/018; A61B 1/2676; A61B 5/08; A61B 5/4836; A61B 2034/107; A61B 2034/2051; A61B 5/062; A61M 1/008; A61M 25/0068; A61M 25/10; A61M 39/24
USPC .................................................. 600/529–543
See application file for complete search history.

(56) References Cited

U.S. PATENT DOCUMENTS 6,287,290 B1  9/2001 Perkins et al.
6,398,775 B1  6/2002 Perkins et al.
(Continued)

FOREIGN PATENT DOCUMENTS

WO       0247748 A1   6/2002
WO    2016109437 A1   7/2016

OTHER PUBLICATIONS

International Search Report dated Nov. 13, 2017 issued in corresponding PCT Application No. PCT/US2017/045037.

*Primary Examiner* — Navin Natnithithadha

(57) ABSTRACT

A system and method enabling the receipt of image data of a patient, identification of one or more locations within the image data illustrating the effects of COPD, planning a pathway to the one or more locations, navigating an extended working channel to one of the locations, positioning a catheter proximate the location, and temporarily evacuating air from within a portion of a patient's lungs including the identified location illustrating the effects of COPD to temporarily isolate the portion of the lungs including the one or more actual locations.

20 Claims, 6 Drawing Sheets

(56) References Cited

U.S. PATENT DOCUMENTS

| | | |
|---|---|---|
| 6,592,594 B2 | 7/2003 | Rimbaugh et al. |
| 6,599,311 B1 | 7/2003 | Biggs et al. |
| 6,984,214 B2 | 1/2006 | Fowler-Hawkins |
| 7,011,094 B2 | 3/2006 | Rapacki et al. |
| 7,100,616 B2 | 9/2006 | Springmeyer |
| 7,533,671 B2 | 5/2009 | Gonzalez et al. |
| 7,798,147 B2 | 9/2010 | Hendricksen et al. |
| 8,136,526 B2 | 3/2012 | Perkins et al. |
| 8,409,168 B2 * | 4/2013 | Wondka ........... A61B 17/12022 604/514 |
| 8,425,455 B2 | 4/2013 | Nentwick |
| 8,474,460 B2 | 7/2013 | Barrett et al. |
| 2003/0164168 A1 | 9/2003 | Shaw |
| 2005/0016530 A1 * | 1/2005 | McCutcheon ... A61B 17/12022 128/200.24 |
| 2005/0033310 A1 | 2/2005 | Alferness et al. |
| 2005/0066974 A1 | 3/2005 | Fields et al. |
| 2006/0162731 A1 * | 7/2006 | Wondka ........... A61B 17/12022 128/207.14 |
| 2009/0255537 A1 | 10/2009 | Shaw et al. |
| 2009/0306545 A1 * | 12/2009 | Elsakka ............ A61M 16/0463 600/581 |
| 2010/0175693 A1 * | 7/2010 | Wondka ........... A61B 17/12022 128/200.24 |
| 2011/0301483 A1 * | 12/2011 | Beyhan .................. A61B 5/082 600/532 |
| 2014/0142376 A1 * | 5/2014 | Ghosh .................... A61B 1/018 600/104 |
| 2016/0184013 A1 * | 6/2016 | Brannan ............ A61B 18/1815 600/424 |

\* cited by examiner

FIG. 3A                    FIG. 3B

INDUCED ATELECTASIS AND PULMONARY CONSOLIDATION SYSTEMS AND METHODS

BACKGROUND

Technical Field

The present disclosure relates to surgical systems, and more particularly, to systems and methods of inducing atelectasis or pulmonary consolidation.

Description of Related Art

Tens of millions of people suffer from lung disease, such as emphysema, chronic obstructive pulmonary disease ("COPD"), asthma, or cancer. Diseases such as emphysema result in poor airflow due to a breakdown of lung tissues. In patients suffering from emphysema the alveoli are no longer elastic and can become enlarged due to walls between the alveoli breaking down. As a result, the alveoli lose their shape and become floppy. This damage from emphysema leads to fewer and larger air sacs instead of many tiny ones. These large alveoli may be called bullae. One result of this breakdown of the alveoli is that the relative amount of gas exchange that can occur in a given unit of time is reduced as the surface area of these fewer enlarged alveoli is less than the many smaller alveoli. Additionally, the weakened floppy alveoli expand during an inhalation. Because of the weakened condition, the air having entered the weakened alveoli cannot be forced out of the lungs during exhalation as a consequence of the decreased elastic recoil of the lungs resulting in the collapse of airways in front of or more proximal to these diseased areas, thus trapping the air in the weakened alveoli. The trapped and thus, deoxygenated, air merely occupies space in the chest and takes up precious volume in the chest cavity that might otherwise be used for gas exchange. As a consequence, the volume available for effective gas exchange of oxygen and carbon dioxide in the chest decreases, thereby resulting in substantive clinical effects such as hypoxemia or on occasion, hypercarbia A patient suffering from emphysema will typically appear thin, and take more rapid, albeit lower volume, breaths. However, those breaths will occur at higher volumes thus further creating a mechanical disadvantage for the respiratory muscles thereby further exacerbating the clinical problems. As can be imagined, the problem of easy filling and poor emptying of the lung leads to progressive hyperexpansion of the lungs, increased residual volume, reduced capacity, inefficient breathing mechanics, and in general, a continually worsening patient condition as they struggle to breathe. The classic description is that the patient will appear as a "pink puffer," because the patient will be constantly working in an effort to inspire any oxygen into their over-inflated lung tissues.

Chronic bronchitis is the result of excessive mucus build-up in the bronchioles. Often this mucus production is part of an inflammatory response caused by injury to the airways from smoking and other inhaled antagonists. The mucus can be so excessive that it overcomes the ability of the cilia within the lungs to sweep the mucus out and allow it to be expelled. Further, the mucus limits the size of the airways through which air must travel in the lungs, thus limiting the volume of air that can be inhaled. The combined effect causes a sufferer to persistently cough in a futile attempt to clear the mucus. This mucus can be so excessive that as it is drawn further and further distal in the lungs (e.g., to the alveoli which might not themselves be inflamed) the mucus limits the gas exchange as it coats the alveoli walls. The mucus reaching the alveoli further exacerbate the challenges of gas transfer experienced by smokers, where tar and other contaminates may already be covering the lining of the alveoli creating a barrier for gas exchange. Further, the mucus and other contaminants are a breeding ground for bacterial growth, promoting further infection and even greater bronchitis symptoms. The classic description of someone suffering from chronic bronchitis is a "blue bloater." The color refers to the lack of oxygen successfully transferring form the alveoli to the blood stream and $CO_2$ being expelled from the blood stream through the alveoli to the atmosphere. These patients often appear bloated due to the elevation of carbon dioxide in the blood as well as the decreased oxygen content in the context of water retention as a result of their compromised pulmonary and circulatory functions. As will be appreciated, many if not most patients will suffer from both emphysema issues and chronic bronchitis issues.

Fully functioning alveoli can often adapt and at least partially compensate for the reduction in total lung capacity caused by emphysema COPD. Indeed, this is one reason for the highly invasive Lung Volume Reduction Surgery (LVRS), where the top portions of the lungs are removed in the hope that the remaining tissue will allow the lung to function more efficiently. In part, this improved performance is enabled by the increase in space afforded to the remaining alveoli as well as to improve the mechanics of the respiratory muscles when these portions of the lung are removed. By reducing the lung size, the remaining lung and surrounding muscles (intercostal and diaphragm) are able to work more efficiently. This makes breathing easier and helps patients achieve greater quality of life.

Aside from the highly invasive LVRS, the standard of care for lung diseases, such as asthma and COPD including emphysema and chronic bronchitis has been focused largely on pharmaceutical treatment modalities. For example, ADVAIR®, a bronchodilator is currently marketed by GlaxoSmithKline plc. for the treatment of COPD. Again, surgical treatment is invasive and alternative approaches such as denervation can result in the disablement of whole or parts of functions of the nerve that affects contraction of the damaged alveoli.

While these treatment options are effective to a point, the primary prescription for patients suffering from COPD is simply the administration of oxygen. Oxygen can alleviate some symptoms but does nothing to treat the underlying diseases.

Further, the highly invasive procedures described above may give rise to myriad complications due to insufficient data available to clinicians regarding the effectiveness of the treatment correlated to patient data. Without sufficient data, and outside of the certain, quite limited, subgroups of patients, clinicians are unable to predict the effectiveness or consequences of the procedure which can be, as mentioned, quite invasive and in certain cases worsen outcomes. Accordingly, a need for an improved method of determining and predicting the effectiveness of lung resection is needed.

SUMMARY

The present disclosure is directed to a system including a memory storing one or more images of a patient and one or more software applications and a display configured to present the one or more images of a patient. The display also configured to present a user interface in combination with the one or more images of a patient enabling the identification of one or more image locations illustrating the effects of chronic obstructive pulmonary disease (COPD). The system further includes an extended working channel navigable to one or more actual locations within the patient corresponding to the one or more image locations, an electromagnetic field generator, and a first sensor associated with the extended working channel, the first sensor detecting a field produced by the electromagnetic field generator. The sensed field enables determination of the location of the first sensor in the electromagnetic field. The system also includes a processor, executing one of the one or more software applications to register the one or more images of a patient with the determined location of the first sensor such that the determined location of the first sensor is presented on the user interface, and a catheter, extendible through the extended working channel and configured to evacuate air from within a portion of a patient's lungs including the one or more actual locations within a patient corresponding to the one or more image locations illustrating the effects of COPD to temporarily isolate the portion of the lungs including the one or more actual locations.

In a further aspect, the system may include an endobronchial valve deployable by the catheter to temporarily induce atelectasis of the portion of a patient's lungs including the one or more actual locations within a patient corresponding to the one or more image locations illustrating the effects of COPD.

In yet another aspect, the system may include a distal balloon disposed on a distal portion of the catheter and expandable to temporarily seal the portion of a patient's lungs including the one or more actual locations within a patient corresponding to the one or more image locations illustrating the effects of COPD.

In a further aspect, the catheter may include a lumen defined therethrough such that air may be evacuated from the sealed portion of the patient's lungs to temporarily induce atelectasis.

In another aspect, the catheter may include a lumen defined therethrough such that fluid is injected through the lumen and into the sealed portion of a patient's lungs to evacuate air from the sealed portion of a patient's lungs to temporarily induce pulmonary consolidation.

In another aspect, the catheter may include a tapered distal tip, the tapered distal tip capable of being wedged within an airway of a patient's lungs to temporarily seal the portion of a patient's lungs including the one or more actual locations within a patient corresponding to the one or more image locations illustrating the effects of COPD.

In yet another aspect, the catheter may include a lumen defined therethrough such that air may be evacuated from the sealed portion of a patient's lungs to temporarily induce atelectasis.

In another aspect, evacuating air from within a portion of a patient's lungs including the one or more actual locations within a patient corresponding to the one or more image locations illustrating the effects of COPD may temporarily induce atelectasis.

In a further aspect, evacuating air from within a portion of a patient's lungs including one or more actual locations within a patient corresponding to the one or more image locations illustrating the effects of COPD may temporarily induce pulmonary consolidation.

A further aspect of the present disclosure is directed to a method enabling the receipt of image data of a patient, identification of one or more locations within the image data illustrating the effects of chronic obstructive pulmonary disease (COPD), planning a pathway to the one or more locations within the image data, navigating an extended working channel to one of the one or more locations within the image data, extending a catheter within the extended working channel and positioning the catheter proximate one of the one or more locations within the image data, temporarily isolating a portion of a patient's lungs including the location illustrating the effects of COPD, and temporarily evacuating air from within the isolated portion of a patient's lungs including the location illustrating the effects of COPD.

In yet another aspect, temporarily isolating a portion of a patient's lungs may include deploying an endobronchial valve to temporarily induce atelectasis of a portion of a patient's lungs including the location illustrating the effects of COPD.

In a further aspect, temporarily isolating a portion of a patient's lungs may include inflating a balloon disposed on a distal portion of the catheter to seal a portion of a patient's lungs including the location.

In yet another aspect, temporarily evacuating air from within the isolated portion of a patient's lungs may include evacuating air via a lumen defined through the catheter to induce atelectasis of the isolated portion of a patient's lungs.

In accordance with a further aspect, temporarily evacuating air from within the isolated portion of a patient's lungs may include injecting a fluid through a lumen defined through the catheter and into the isolated portion of a patient's lungs.

In another aspect, temporarily isolating a portion of a patient's lungs may include wedging a tapered distal tip defined on a distal portion of the catheter against an airway of a patient's lungs to seal a portion of a patient's lungs including the location.

In yet another aspect, temporarily evacuating air from within the isolated portion of a patient's lungs may include evacuating air via a lumen defined through the catheter to temporarily induce atelectasis of the isolated portion of a patient's lungs.

In still another aspect, temporarily evacuating air from within the isolated portion of a patient's lungs may include injecting fluid through a lumen defined through the catheter and into the isolated portion of a patient's lungs to induce pulmonary consolidation of the isolated portion of a patient's lungs.

In yet another aspect, evacuating air from within the isolated portion of a patient's lungs including the location illustrating the effects of COPD may induce one of atelectasis or pulmonary consolidation within the isolated portion of a patient's lungs.

In a further aspect, the method may further include predicting the clinical consequences of temporarily inducing atelectasis of a portion of the lungs including the location illustrating the effects of COPD.

BRIEF DESCRIPTION OF THE DRAWINGS

Various aspects and features of the present disclosure are described hereinbelow with references to the drawings, wherein:

FIG. 3A is a side view of a distal portion of the tool of FIG. 3;

FIG. 3B is an enlarged view of the isolated portion of a patient's lungs illustrating a fluid being injected by the tool of FIG. 3;

DETAILED DESCRIPTION

Figure 1:
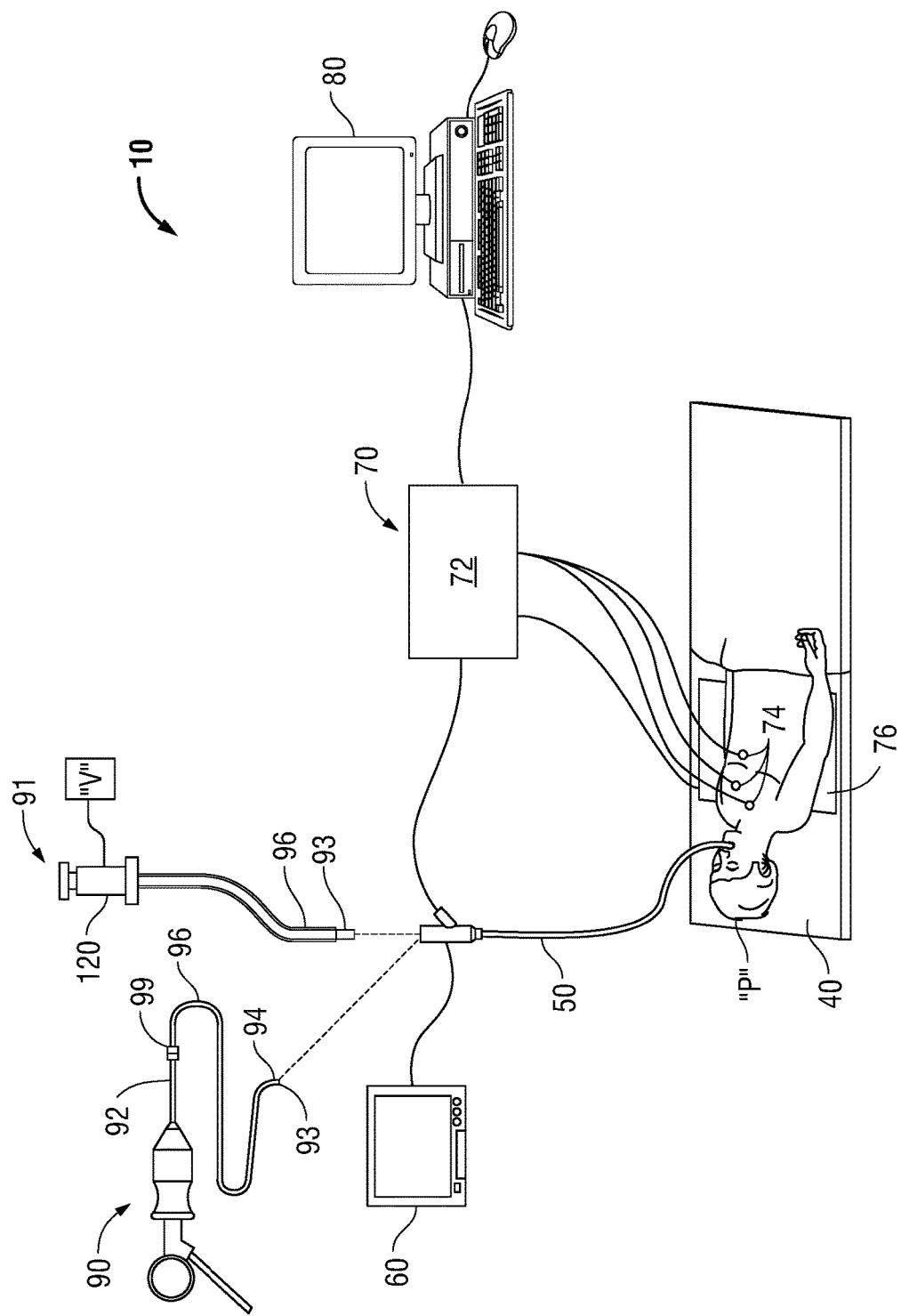
FIG. 1 is a perspective view of a system provided in accordance with the present disclosure configured for navigating a tool to an area of interest and inducing atelectasis or pulmonary consolidation.

The present disclosure is directed to devices and systems for irreversibly or reversibly inducing atelectasis or pulmonary consolidation in a patient as part of a process of evaluating the effects of a permanent treatment. As described herein, one or more airway closure or instillation devices may be navigated to a location within the airways and deployed to isolate a particular portion of the lungs, in some instances, through the use of an Electromagnetic Navigation (EMN) System. The air within the isolated portion of the lungs can be removed by application of a vacuum or by the lungs forcing the air out via a one-way valve (such as an endobronchial valve or the like). The evacuation of the isolated portion of the lungs causes the isolated portion to collapse, thus reducing the volume of the chest cavity the evacuated portion of the lung occupies. Alternatively, a fluid such as a liquid, gas, or other substance may be injected within the lungs to displace the air within the isolated portion of the lungs, thereby inducing pulmonary consolidation in the isolated portion of the lung. As described herein, this reversible isolation enables a clinician to observe the effects of such an isolation and reduction in volume, and be able to determine both whether such a reduction will result in an improvement in lung function for the patient, have deleterious effects, and also whether a surgical or other permanent lung volume reduction or treatments directed at that location would be effective. Over time, a database may be built using the data obtained during each reversible isolation procedure. This database may be indexed such that clinicians may review data obtained from similar patients to better predict the outcome of the procedure. As can be appreciated, each of the procedures detailed herein may be reversible or irreversible. Further, it is envisioned that the reversible procedures may be converted to an irreversible procedure upon determining whether isolating the particular portion of the lung provides the desired results.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

With reference to FIGS. 1-4, a method of temporarily isolating a portion of a patient's lung using an endoscopic approach is described. Initially, patient characteristics are recorded in a memory coupled to a computer 80 (FIG. 1). The memory may include any non-transitory computer-readable storage media for storing data and/or software that is executable by a processor (not shown), e.g., solid-state, volatile, non-volatile, removable, and non-removable. Patient characteristics may include, but are not limited to, age, sex, race, lung volume, disease type, respiration rate, observed overinflation, smoking history, oxygen saturation, or the like. Next, the patient is imaged using any suitable imaging device (not shown), such as MRI, ultrasound, CT scan, Positron Emission Tomography (PET), metabolic scanning, or the like, and the images are stored within the memory coupled to computer 80 (FIG. 1). As can be appreciated, the image obtained by the imaging device may be correlated or indexed to patient data to enable a clinician to look-up similarly situated patients. In this manner, the clinician may better predict the clinical consequences of isolating the particular portion of the patient's lungs, as will be described in further detail hereinbelow.

Following imaging, a software application may be initiated to enable review of the image data. One example of such an application is the ILOGIC® planning and navigations suites currently marketed by Medtronic. An area of interest illustrating the effects of lung disease (e.g., emphysema, COPD, asthma, cancer, or the like) is identified in the images and its location determined within the lungs of the patient. Several methods of identifying an area of interest are contemplated such as ultrasound, CT scan, metabolic scanning, or the like. In one non-limiting embodiment, where the patient is not suffering from easily identified lesions or cancers of the lungs, the results of images generated from a CT scan can be analyzed to identify areas of hypodensity. Hypodense portions of the lungs are areas where the density of the tissue is less than the surrounding tissue. This may be particularly useful for patients suffering from emphysema as the expanded floppy alveoli or bullae will provide images that have areas which may be substantially darker or blacker that the surrounding tissue, indicating that they are largely air with little to no tissue separating these enlarged alveoli. Because of this hypodensity, image analysis using 3D image processing is particularly useful as identification of the areas where the densities of the images (measured in Hounsfield units or HU) is below a certain threshold (e.g. −950 HU) approximately the same as air. This 3D rendering is relatively straightforward and even coarse thresholding can be employed to distinguish the enlarged alveoli from tissue and identify their locations in the CT images. These coarse threshold values can then be rendered as a 3D model of the affected areas of the lungs. Techniques for generating 3D volumetric renderings are described in U.S. patent application Ser. No. 14/821,950 to Bharadwaj et al. entitled "Treatment Procedure Planning System and Method," filed Aug. 10, 2015, the entire contents of which are incorporated by reference herein. In an alternative embodiment, PET imaging may be utilized to identify areas of low metabolic activity within the lungs. As can be appreciated, a device capable of performing a combined PET/CT imaging technique may be utilized, which has proven to be quite accurate. These areas of very little metabolic activity should closely correspond to areas of overinflated alveoli. There is very little metabolic activity in these areas because they are mostly comprised of air. In this way, a PET image set can be utilized to identify the hypodense areas to which navigation and treatment should be directed. After careful analysis, using one of the above described techniques, the location of the area of interest may be identified and its location stored within the memory coupled to computer 80 (FIG. 1).

Next, the clinician utilizes the software to determine a pathway through the liminal network of the lungs to the area of interest. Thereafter, the clinician enters the navigation phase. A bronchoscope 50 (FIG. 1) is inserted within the patient and navigated through the patient's airways and adjacent the area of interest using a tracking system 70 (FIG. 1). However, if bronchoscope 50 is unable to be navigated to the area of interest due to the size of bronchoscope 50 prohibiting further insertion, a LG 92 and a EWC 96 (FIG. 1) may be advanced within a working channel of bronchoscope 50 and independently navigated to the area of interest via tracking system 70. As can be appreciated, any suitable navigation and/or tracking system may be utilized to navigate the LG 92 and EWC 96 to the area of interest.

Figure 2:
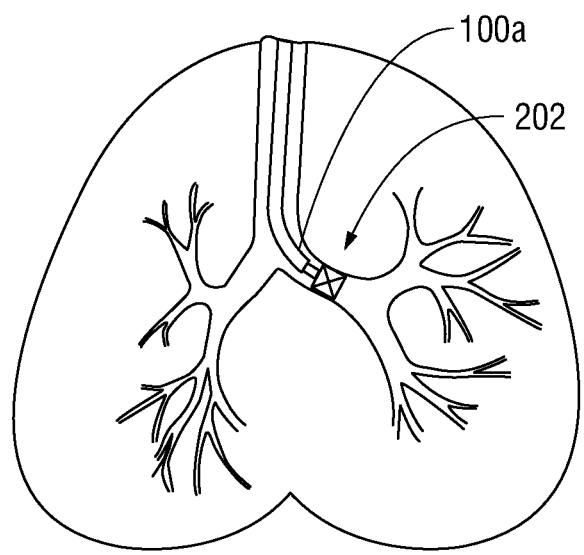
FIG. 2 is a front, cross-sectional, view of the lungs of a patient including a one-way valve disposed within an airway of the lungs.

Once the EWC 96 is placed proximate the area of interest, the LG 92 may be removed from EWC 96 and a mechanism for isolating the airway may be inserted in the EWC 96. One example of a mechanism for isolating the airway is an endobronchial valve 202 as shown in FIG. 2. Typically, endobronchial valves are one-way valves which only permit air to be exhaled from an isolated portion of the lung and do not permit inhalation into the isolated portion of the lungs. To deploy an endobronchial valve 202, the endobronchial valve 202 is placed in a catheter or tool 100a and once at the area of interest, the endobronchial valve 202 is ejected from the catheter 100a using, for example, a simple push rod (not shown). The endobronchial valve 202 may be formed of a shape memory material (i.e., shape memory alloy or shape memory polymer) such that once ejected from the catheter the valve expands to seal the airway. Central to the endobronchial valve 202 may be a duckbill type valve mechanism which permits only one way airflow. As can be appreciated, catheter 100a may be advanced within EWC 96.

Figure 2A:
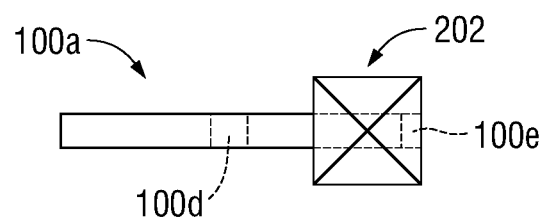
FIG. 2A is a side view of a tool capable of placing the one-way valve of FIG. 2 within an airway of the lungs.
Figure 2B:
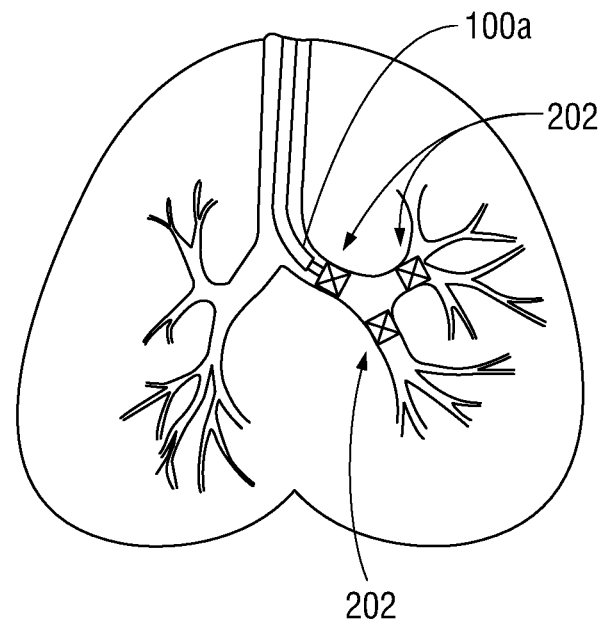
FIG. 2B is a front, cross-sectional, view of the lungs of a patient including a plurality of one-way valves disposed within a corresponding plurality of airways of the lungs.

Endobronchial valve 202 is temporarily secured within the airway such that air may escape those portions of the lungs distal the valve (i.e., the area of the lung including the area of interest), but no new air may be drawn in those portions of the lung. In this manner, atelectasis, collapsing the affected portion of the lung including the area of interest, is induced. In some instances, due to a condition known as collateral ventilation, it may be necessary to place multiple endobronchial valves 202 within the affected portion of the lung in order to isolate the desired portion of the lung. In this manner, a plurality of endobronchial valves 202 may be placed within one or more airways (FIG. 2B) in order to effectively evacuate air within the isolated portion of the lung. Indeed, the use of the endobronchial valves 202 may provide the ability to perform important diagnostics on the conditions of the lungs before any surgery is performed, as will be described in further detail hereinbelow.

In another embodiment, the airway may be isolated by means of a balloon catheter or tool 100b including balloon 302 (FIG. 3) or other closure device disposed on an exterior surface thereof. In this manner, the balloon catheter 100b may be introduced within EWC 96 and advanced to a suitable location adjacent the area of interest, at which point the balloon 302 may be inflated by means of a pump, syringe, or other suitable device in fluid communication therewith (not shown). As a result of the inflation, an exterior surface 304 (FIG. 3A) of the balloon 302 expands and compresses against the inner walls of the airway. In this manner, the portion of the lungs containing the area of interest is sealed off from the remaining portions of the lung. It is contemplated that the air contained within the isolated portion of the lung may be evacuated through a cannula 306 (FIG. 3A) defined through balloon catheter 100b using any suitable means, such as a vacuum or the like (not shown), to induce atelectasis. As can be appreciated, balloon catheter 100b may be any suitable balloon catheter known in the art capable of being advanced within a working channel of a bronchoscope or EWC.

It is contemplated that the balloon catheter 100b may be utilized to inject a fluid such as a liquid or gas or other substance (e.g., saline or the like) within the isolated portion of the lungs to displace the air from the isolated portion of the lung and induce pulmonary consolidation (FIG. 3B). In this manner, the balloon catheter 100b may be in fluid communication with a fluid reservoir (not shown) and fluid pump (not shown) or other suitable device capable of injecting fluid through the cannula 306 (FIG. 3A) of the balloon catheter 100b and into the isolated portion of the lungs. As can be appreciated, the pump or other device can be reversed, such that the fluid that has been injected within the lung may be evacuated. In some embodiments, the balloon catheter 100b may include a second lumen (not shown) defined therethrough to allow the air within the isolated portion of the lung to be displaced as the fluid is injected therein.

Figure 3:
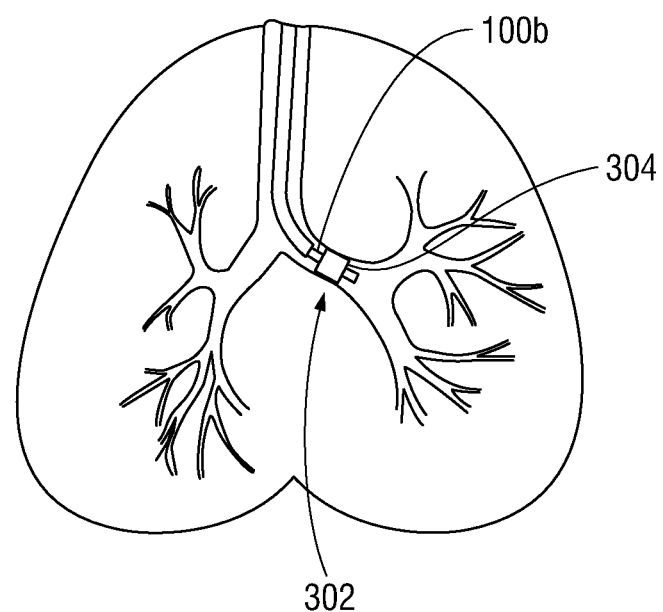
FIG. 3 is a front, cross-sectional, view of the lungs of a patient including a tool including a balloon inflated to isolate a portion of the lungs.
Figure 3C:
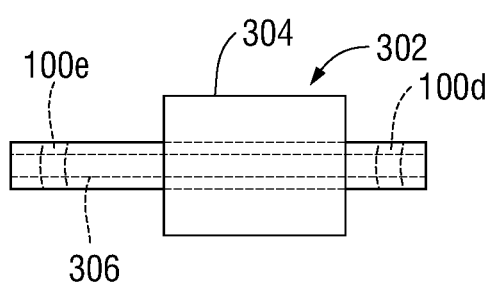
FIG. 3C is a front, cross-sectional, view of the lungs of a patient including an alternate embodiment of the tool of FIG. 3A.
Figure 3C:
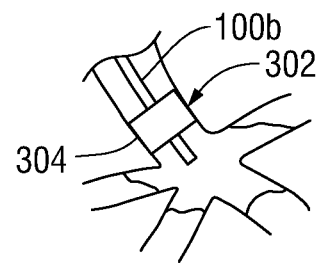
Figure 3C:
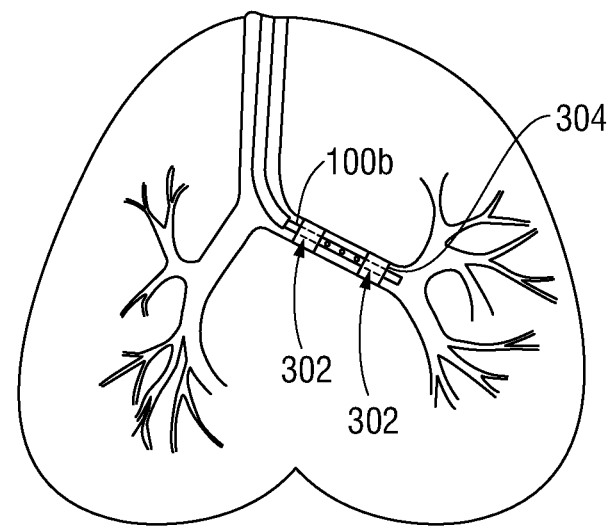
Figure 3D:
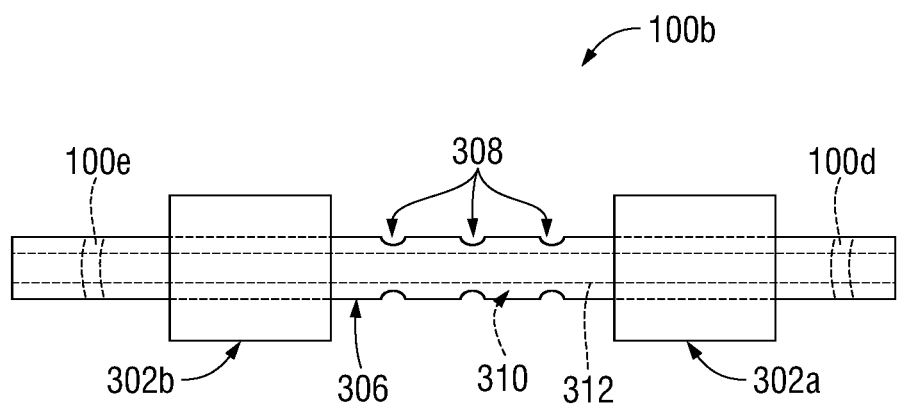
FIG. 3D is a side view of a distal portion of the tool of FIG. 3C.
Figure 3E:
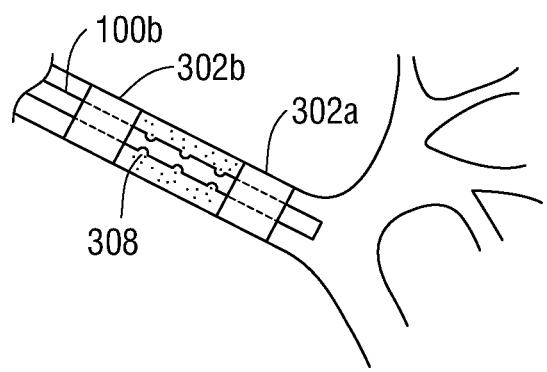
FIG. 3E is an enlarged view of the isolated portion of a patient's lungs illustrating a fluid being injected by the tool of FIG. 3C.

With reference to FIGS. 3C-3E, it is contemplated that the tool 100b may include a pair of balloons 302a and 302b disposed on an outer surface thereof, although it is contemplated that any suitable number of balloons may be disposed on the outer surface of the tool 100b depending on the needs of the procedure being performed. As best illustrated in FIG. 3D, the pair of balloons 302a, 302b is disposed in spaced relation to one another such that a first balloon 302a is disposed distal of a second balloon 302b of the pair of balloons 302a, 302b. In this manner, the pair of balloons 302a, 302b may isolate a portion of the patient's lungs therebetween, allowing for a more focused area of treatment. As can be appreciated, each balloon of the pair of balloons 302a, 302b may be separated from the other by any suitable distance, depending on the size of the area of interest and the procedure being performed.

A plurality of radial orifices 308 (FIG. 3D) is defined through the portion of the catheter 306 disposed between the pair of balloons 302a, 302b. The plurality of radial orifices 308 are in fluid communication with a first lumen 310 disposed within the cannula 306 of the tool 100b separate from a second lumen 312 disposed within the cannula 306, although it is contemplated that the second lumen 312 may be disposed within the first lumen 310 such that the second lumen 312 and the first lumen 310 are concentrically disposed within the catheter 306. In one non-limiting embodiment, the interior portion of the catheter 306 is hollow, defining the first lumen 310, and the second lumen 312 is disposed therewithin in a similar manner as described above. The first lumen 310 is in fluid communication with a pump, syringe, or other suitable device capable of either evacuating the air contained within the portion of the lungs isolated by the pair of balloons 302a, 302b or injecting a fluid therewithin (FIG. 3E), similarly to that described above. As can be appreciated, the second lumen 312 may be utilized to permit air to flow to and from the portion of the patient's lungs distal of the first balloon 302a (i.e., the distal-most balloon), thereby ensuring that the only portion of the patient's lung that is evacuated of air is located between the pair of balloons 302a, 302b. It is envisioned that a third lumen (not shown) may be disposed within the catheter 306 to allow the air within the isolated portion of the lung to be displaced as the fluid is injected therein.

Figure 4:
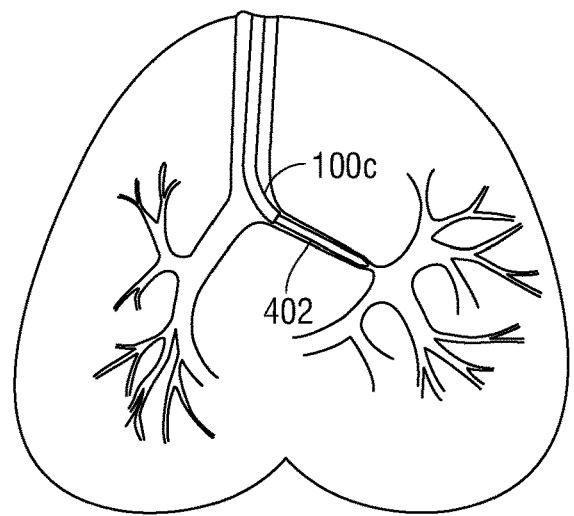
FIG. 4 is a front, cross-sectional, view of the lungs of a patient including a tool having a tapered distal tip.
Figure 4A:
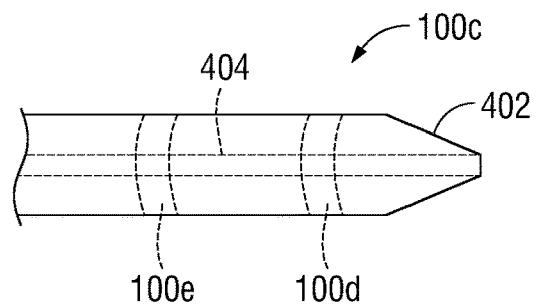
FIG. 4A is a side view of a distal portion of the tool of FIG. 4.

In a further embodiment, it is contemplated that a catheter or tool 100c having a tapered distal tip 402 (FIGS. 4 and 4A) may be advanced within EWC 96 and, thereafter, the airways of the patient until the tapered distal tip 402 is wedged against the inner walls of the patient's airway. In this manner, the outer diameter of the tapered distal tip 402 is compressed against the inner wall of the patient's airway until the tapered distal tip 402 is sealed thereagainst. Again, tool 100c may include a lumen 404 (FIG. 4A) defined therethrough in fluid communication with a pump, vacuum, or other similar device (not shown) capable of evacuating air or liquid. The air within the isolated portion of the lungs may be evacuated, thereby inducing atelectasis.

Figure 4B:
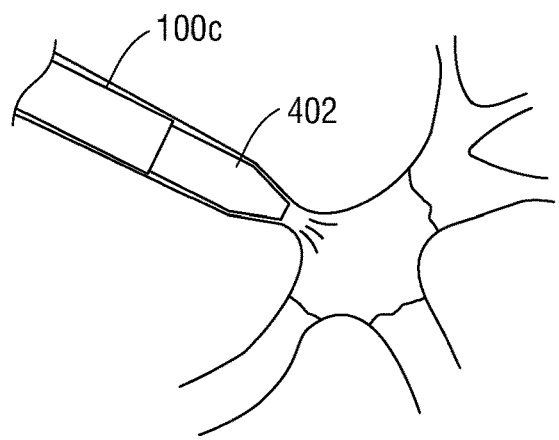
FIG. 4B is an enlarged view of the isolated portion of a patient's lungs illustrating a fluid being injected by the tool of FIG. 4.

It is contemplated that tool 100c may be utilized to inject a fluid such as a liquid or gas or other suitable substance (e.g., saline or the like) into the isolated portion of the lung (FIG. 4B) in a similar manner as described above with respect to balloon catheter 100b. In this manner, after the tapered distal tip 402 is sealed against the inner wall of the patient's airways (FIG. 4), the fluid may be injected within the isolated portion of the lung using a fluid reservoir (not shown) and a pump (not shown) or other device capable of injecting fluid through the lumen 404 (FIG. 4A) of the tool 100c and into the isolated portion of the lungs. As can be appreciated, the pump or other device can be reversed, such that the fluid that has been injected within the lung may be evacuated. In some embodiments, the tool 100c may include a second lumen (not shown) defined therethrough to allow the air within the isolated portion of the lung to be displaced as the fluid is injected therein.

As can be appreciated, a clinician may isolate as many portions of the lung as necessary in order to obtain the desired results. In this manner, a clinician may isolate each portion of the lung by only atelectasis, by only pulmonary consolidation, or using a combination of atelectasis and pulmonary consolidation (i.e., a first portion of the lung may be isolated by atelectasis and a second portion of the lung may be isolated by pulmonary consolidation).

In embodiments, each of the one way valve 100a, balloon catheter 100b, and tool 100c may include a pressure sensor 100e (FIGS. 2A, 3A, and 3C) or other suitable device disposed thereon capable of measuring the pressure within the isolated portion of the lung, such as a digital or analog sensor (piezoelectric, capacitive, electromagnetic, optical, piezoresistive, resonant, thermal, or the like). As can be appreciated, the pressure sensor 100e may be wireless and communicate with the computer 80 or monitoring equipment 60 (FIG. 1). In embodiments, the pressure sensed by the pressure sensor 100e may be displayed on a standalone display (not shown) or may be shown in a display monitor associated with the computer 80 (FIG. 1).

The pressure sensor 100e is in fluid communication with the isolated portion of the lung via one way valve 100a, cannula 306 of the balloon catheter 100b, or lumen 404 of the tool 100c. It is contemplated that the pressure sensor 100e may be located remote from the one way valve 100a, balloon catheter 100b, and tool 100c. In this manner, a conduit (not shown) or other similar device couples the pressure sensor 100e to the one way valve 100a, balloon catheter 100b, or tool 100c such that the sensor 100e is in fluid communication with the isolated portion of the lung.

As can be appreciated, the accuracy of the results obtained during the procedure described below depends on whether the isolated portion of the lung has been entirely evacuated of air. Therefore, it is important that the clinician is able to verify that the isolated portion of the lung has been entirely evacuated of air. In this manner, the pressure sensor 100e may be utilized to ensure that the isolated portion of the lung has been completely evacuated of air before continuing with other aspects of the procedure. It is envisioned that other modalities may be used to ensure that the isolated portion of the lung has been completely evacuated of air, such as ultrasound, measuring impedance characteristics, physical measurements, imaging modalities such as MRI, PET, or the like. When completely evacuated of air, the isolated portion of the lung will appear lighter in color than the surrounding portions in the images obtained by the imaging modality. In this manner, the clinician is able to readily determine whether or not the isolated portion of the lung has been entirely evacuated of air.

In embodiments, it is contemplated that LG 92 be eliminated and tool 100 itself is utilized for navigation, similarly as detailed above with respect to LG 92. In this manner any of the above tools 100a, 100b, 100c, may include a sensor 100d (FIGS. 2A, 3A, and 4A) that, in conjunction with tracking system 70 (FIG. 1), may be employed to enable tracking of a distal portion of tools 100a, 100b, 100c, as the distal portion of tools 100a, 100b, 100c is advanced through the patient's airways, as detailed above. Thus, with additional reference to FIG. 1, computer 80, monitoring equipment 60, and/or any other suitable display may be configured to display the three-dimensional model and selected pathway, both of which were generated during the planning phase (as detailed above), along with the current location of the sensor disposed in the distal portion of tools 100a, 100b, 100c to facilitate navigation of the distal portion of tools 100a, 100b, 100c to the area of interest and/or manipulation of the distal portion of tools 100a, 100b, 100c relative to the area of interest. Alternatively, tools 100a, 100b, 100c may not include a sensor and, rather, only LG 92 may be utilized for navigation and position.

Continuing with FIGS. 1-4, it is contemplated that a predictive approach may be utilized. Such an approach may better enable a clinician to determine whether the planned procedure will have the desired outcome or will result in deleterious effects. In this manner, the clinician initially records patient data corresponding to the patient's vitals, such as pulmonary function (through a Pulmonary Function Test, blood gas analysis, or the like), cardiac function (i.e., heart rate or the like), respiration rate, oxygen saturation, and breathing effort and enters this information into a database. Additionally, identifying information such as age, sex, height, weight, race or national origin, or the like, disease type and planned procedure, in addition to the patient's medical history is recorded. Over time, a database may be built using the data obtained during each procedure. This database may be indexed such that clinicians may review data obtained from similar patients to better predict the outcome of the procedure.

In further embodiments, it is contemplated that images of the patient obtained by a suitable imaging device may be correlated or indexed to patient data to enable a clinician to look up similarly situated patients. In this manner, the clinician may better predict the clinical consequences of the planned procedure, as will be described in further detail hereinbelow.

After performing a temporary or permanent procedure, the clinician observes the patient to determine the clinical consequences of inducing atelectasis and/or pulmonary consolidation of the portion or portions of the lung including the area of interest. In this manner, the clinician may monitor the patient's heart rate, respiration rate, oxygen saturation, breathing effort, or other vital signs indicative of whether the procedure has improved the patient's condition, maintained the patient's condition, or degraded the patient's condition. Using this information, the clinician determines whether isolating the portion of the lung produced the desired clinical effect. Some of these effects may be immediately apparent while others may require some time to materialize. For example, the induced atelectasis or pulmonary consolidation and the resultant increase in available volume for functioning lung tissue to expand should immediately result in changes in the blood oxygenation levels as more air is able to be brought into the lungs. Nevertheless, sometimes these changes are not immediately apparent and thus once the patient is allowed to awaken from the procedure in the situation where an evaluation of the effect of the isolation is necessary, a clinical assessment using both qualitative and quantitative measures can be undertaken. The clinician may record the clinical effects of the procedure in the database stored in the memory of the computer 80 (FIG. 1). In this manner, the location where the portion of the lung was isolated is recorded in the memory and correlated to the location of the area of interest and the clinical record of the patient. It is further contemplated that the type of treatment being proposed, the volume of the treatment area including the amount of tissue being treated, the type of tissue being targeted, dynamic measures of integrated function (e.g., the six minute walk test), and qualitative metrics (e.g., St. Georges Respiratory Questionnaire) may be recorded and correlated to the patient data.

By recording the above described information, the clinical consequences of the procedure are made accessible by clinicians performing similar procedures in the future, and may be used to predict the clinical effect of similar procedures in the future. As can be appreciated, once the database is populated with a number of procedures and/or patients, a clinician will be able to predict or otherwise determine whether the planned procedure would produce the desired clinical effects. For example, a patient suffering from emphysema affecting a portion of the lungs located in the upper portion of the right lobe may be correlated to a similar patient having emphysema affecting a portion of the lungs located in the upper portion of the right lobe whose data has been entered into the database. In this manner, the clinician is able to predict whether the planned procedure would produce the desired clinical effects. Indeed, by predicting whether a patient would benefit from removal or isolation of a particular portion of the lung, the clinician is able to reduce the number of procedures required to treat the patient (i.e., eliminating or vastly reducing a trial and error approach), thereby reducing pain, recovery time, and expense. Further, this predictive model provides a basis to determine whether a patient's outcome meets the prediction or falls short and if it falls short the clinician may be able to identify one or more aggravating factors not previously contemplated and perform further procedures. The data of these procedures is recorded and used to further the database for future clinicians.

As can be appreciated, if enough data is present, the clinician may skip temporarily isolating of the lungs and perform a permanent resection, thereby subjecting the patient to a minimal amount of procedures to arrive are the desired effect. In some embodiments, after monitoring the clinical effect of temporarily isolating the portion of the lung including the area of interest, the clinician may convert the temporary isolation to a more permanent isolation by leaving the one way valves 202 within the lung, resection, placing claims on the airways, or any other suitable means known in the art.

It is further contemplated that the above detailed predictive approach may be utilized in conjunction with tracking system 70 (FIG. 1) to facilitate navigation of tools 100*a*, 100*b*, or 100*c* to a location adjacent the area of interest and/or tracking of tools 100*a*, 100*b*, or 100*c* as they are manipulated to isolate the portion of the lungs containing the area of interest.

Once the area of interest is identified, the patient is compared to information stored in the database pertaining to other patients using a suitable software application executed by the processor. The process of identifying the area of interest is similar to that described above and, thus, will not be detailed herein for purposes of brevity. The software application compares the current patient's characteristics and the location of the area of interest to the entries populating the database, and using a mathematical computation or other similar means, identifies a particular patient or set of patients to which the current patient substantially aligns. As can be appreciated, the software application may assign a percentage or other identifier (e.g., ranking, number of similar characteristics, or the like) to patients stored within the database, such that the current patient may be considered a 100% match, 95% match, or the like. It is further contemplated that the software application may rank or otherwise compile, in descending or ascending order, a list of identified patients. Using this information, the clinician may make an educated determination as to the likelihood that removing or isolating that particular portion of the lungs would produce the desired clinical effect. With this information available to the clinician during the planning phase, the clinician may make an informed decision to either temporarily isolate the portion of the lungs containing the area of interest, as described hereinabove, or permanently remove the tissue or permanently isolate the portion of the lungs containing the area of interest using any suitable means.

Finally, using the software application described above, the clinician observes the clinical effects similarly to that described above, and thereafter, records the clinical effects of the procedure and enters the information into the database. In embodiments, it is envisioned that the clinician records the clinical effects regardless of whether he chose to permanently isolate or temporarily isolate the portion of the lungs containing the area of interest. This ensures that the database is continually updated such that future clinicians receive the most up to date and reliable information possible when planning future procedures.

Yet a further aspect of the present disclosure is a predictive outcome application. With all the procedures described herein, there will be follow-up CT imaging and most likely pulmonary function testing. These data, particularly the CT image data and particularly contrast enhanced CT imaging or PET/CT imaging, can be collected in an effort to identify the actual outcomes associated with the treatments described herein and at a minimum determine if follow-up procedures are necessary. By comparing actual outcomes to the treatment parameters better guidelines can be given to the clinicians. More importantly the planning software (described above) can rely on this data to adjust the expected treatment zone given a wide array of factors including size of alveolus or lung parenchyma treated, size of blood vessels in the treatment area, location in the lung (e.g., which bifurcation), power and duration of ablation and others. As a result, over time the predictions in the planning software are refined to provide greater accuracy. It is also contemplated that the above described software could alert surgeons and proceduralists to aberrant distributions of the vasculature that would be valuable to know pre-procedurally. In this manner, the identified aberrant distributions could be used to alter operative or procedural planning.

Referring back to FIG. 1, an Electromagnetic Navigation (EMN) system configured for reviewing CT image data (such as that described above with respect to hypodensity identification) to identify one or more areas of interest, planning a pathway to an identified area of interest (planning phase), navigating an extended working channel (EWC) 96 to the area of interest (navigation phase), and utilizing a tool to induce atelectasis (isolation phase) is shown generally identified by reference numeral 10. Once such EMN system is the ELECTROMAGNETIC NAVIGATION BRONCHOSCOPY® system currently sold by Medtronic.

System 10 generally includes an operating table 40 configured to support a patient "P", a bronchoscope 50 configured for insertion through the patient's mount into the patient's airways, monitoring equipment 60 coupled to the bronchoscope 50 for displaying video images received from bronchoscope 50, a tracking system 70 including a tracking module 72, a plurality of reference sensors 74, and a transmitter mat 76; a computer 80 including software and/or hardware used to facilitate navigation and tracking of the bronchoscope within the patient's airways and identification of an area of interest; a positioning assembly 90 or 91 including a locatable guide (LG) 92, and extended working channel (EWC) 96, and tools 100a, 100b, 100c insertable through the positioning assembly 90, 91.

With respect to the planning phase, computer 80 utilizes computer tomographic (CT) image data for generating and viewing a three-dimensional model of the patient's airways, enables the identification of an area of interest on the three-dimensional model (automatically, semi-automatically, or manually), and allows for the selection of a pathway through the patient's airways to the area of interest. More specifically, the CT scans are processed and assembled into a three-dimensional CT volume, which is then utilized to generate a three-dimensional model of the patient's airways. Although the planning phase is generally described as utilizing CT scans, it is contemplated that any suitable imaging means may be utilized, such as Magnetic Resonance Imaging (MRI), Ultrasound, or the like. The three-dimensional model may be displayed on a display monitor associated with computer 80, or in any other suitable fashion. Using computer 80, various views of the three-dimensional model may be provided and/or the three-dimensional model may be manipulated to facilitate identification of an area of interest on the three-dimensional model and selection of a suitable pathway through the patient's airways to access the area of interest. Once selected, the pathway is saved for use during the navigation phase(s). One such planning software is the ILOGIC® planning suite currently sold by Medtronic. Details of such planning software are described in commonly owned and co-pending U.S. Published Patent Application No. 2014/0270441 to Baker entitled "Pathway Planning System and Method" filed Mar. 15, 2013, the entire contents of which are incorporated herein by reference.

Although the apparatus and methods of isolating a portion of the patient's lungs are described as utilizing the planning phase, it is contemplated that the planning phase may be omitted, and just the navigation phase and isolation phase be performed, or alternatively, the isolation phase may be performed utilizing conventional medical equipment and/or without the aid of the planning and navigation phases, such as through the use of imaging modalities (i.e., fluoroscopy or the like.).

With respect to target identification, different from the currently marketed ILOGIC® software, in addition to the capability of reviewing CT images to identify calcifications representing either lesions or tumors, in accordance with the present disclosure, the CT image data, and the software applications for analyzing the CT image data are also capable of detecting and identifying hypodense areas in the CT images, as well as the vasculature, either from 3D image analysis or by incorporating angiogram, CT angiogram data, or PET/CT image analysis. These different data sets, which may be generated from multiple different image sets can either be fused, or layered, or otherwise registered together such that relevant data from each data set can be presented in a useable form enabling identification of the area to be treated (e.g., hypodense areas) as well as the airways leading to that target. In this way, according to the present disclosure the planning software allows the clinician to identify the hypodense areas to target and to incorporate the pathway planning described above, and navigation aspects described below. As can be appreciated, other modalities capable of identifying the area to be treated may be utilized, such as ultrasound, pulmonary function testing, metabolic scanning, or the like.

Referring again to FIG. 1, Patient "P" is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50. In embodiments, it is contemplated that bronchoscope 50 may be any suitable bronchoscope capable of navigating the airways of a patient and permitting a suitable tool 100 to be inserted therein. For a detailed description of an exemplary bronchoscope 50, reference can be made to U.S. Patent Application Publication No. 2015/0265257 to Costello et al. entitled "Devices, Systems, and Methods for Navigating a Biopsy Tool to a Target Location and Obtaining a Tissue Sample Using the Same", filed Dec. 9, 2014, the entire contents of which are incorporated by reference herein.

System 10 includes a navigation system capable of guiding bronchoscope 50 to an area of interest. The navigation system may be a six degrees-of-freedom electromagnetic tracking system 70, e.g., similar to those disclosed in U.S. patent application Ser. No. 14/753,288 to Brown et al. entitled "System and Method for Navigating within the Lung", filed Jun. 29, 2015 and published PCT Application Nos. WO 00/10456 and WO 01/67035, the entire contents of each of which is incorporated herein by reference, or other suitable positioning measuring system, is utilized for performing registration and navigation, although other configurations are also contemplated. Tracking system 70 includes a tracking module 72, a plurality of reference sensors 74, and a transmitter mat 76. Tracking system 70 is configured for use with either positioning assembly 90 or positioning assembly 91, and tools 100a, 100b, 100c, as detailed below. Positioning assemblies 90 and 91 further include an EWC 96 and a handle 98. LG 92 and EWC 96 are configured for insertion through a working channel of bronchoscope 50 into the patient's airways (although LG 92 and EWC 96 may alternatively be used without bronchoscope 50) and are selectively lockable relative to one another via a locking mechanism 99. Distal tip 93 of LG 92 may be configured for steering in any suitable fashion, e.g., using a plurality of steering wires (not shown) coupled between handle 98 and distal tip 93, to facilitate maneuvering distal tip 93 of LG 92 and EWC 96 through the patient's airways. Alternatively, rotation and translation of handle 120 may facilitate maneuvering of the distal tip 93 of LG 92, and in particular embodiments the EWC 96 may be angled or curved to assist in maneuvering the distal tip 93 through the airways. Sensor 94 is integrated with distal tip 93 of LG 92 and allows monitoring of the position and orientation of distal tip 93, in six degrees of freedom, relative to the reference coordinate system. For a detailed description of the construction of exemplary navigation systems, reference may be made to U.S. Patent Application Publication No. 2015/0265257 to Costello et al., incorporated by reference hereinabove.

A transmitter mat 76 is positioned beneath the patient "P" and is a transmitter of electromagnetic radiation. Transmitter mat 76 includes a stack of three substantially planar rectangular loop antennas (not shown) configured to be connected to drive circuitry (not shown). For a detailed description of the construction of exemplary transmitter mats, which may also be referred to as location boards, reference may be made to U.S. Patent Application Publication No. 2009/0284255 to Zur entitled "Magnetic Interference Detection System and Method", filed Apr. 2, 2009, the entire contents of which are incorporated by reference herein.

Transmitter mat 76 and the plurality of reference sensors 74 are interconnected with tracking module 72, which derives the location of each sensor 74 in six degrees of freedom. One or more of reference sensors 74 are attached to the chest of the patient "P." The six degrees of freedom coordinates of reference sensors 74 are sent to computer 80 (which includes the appropriate software) where they are used to calculate a patient coordinate frame of reference. Registration, as detailed below, is generally performed by identifying locations in both the three-dimensional model and the patient's airways and measuring the coordinates in both systems. Further details of such a registration technique can be found in U.S. Patent Application Pub. No. 2011/0085720 to Barak et al. entitled "Automatic Registration Technique", filed May 14, 2010, the entire contents of which are incorporated herein by reference, although other suitable registration techniques are also contemplated.

In use, with respect to the navigation phase, LG 92 is inserted into positioning assembly 90, 91, and EWC 96 such that sensor 94 projects from the distal end of EWC 96. LG 92 and EWC 96 are then locked together via locking mechanism 99 (for example). LG 92, together with EWC 96, are then inserted through bronchoscope 50 and into the airways of the patient "P," with LG 92 and EWC 96 moving in concert with one another through bronchoscope 50 and into the airways of the patient "P." Automatic registration is performed by moving LG 92 through the airways of the patient "P." More specifically, data pertaining to locations of sensor 94 while LG 92 is moving through the airways is recorded using transmitter mat 76, reference sensors 74, and tracking module 72. A shape resulting from this location data is compared to an interior geometry of passages of the three-dimensional model generated in the planning phase, and a location correlation between the shape and the three-dimensional model based on the comparison is determined, e.g., utilizing the software on computer 80. In addition, the software identifies non-tissue space (e.g., air filled cavities) in the three-dimensional model. The software aligns, or registers, an image representing a location of sensor 94 of LG 92 with an image of the three-dimensional model based on the recorded location data and an assumption that LG 92 remains located in non-tissue space in the patient's airways. This completes the registration portion of the navigation phase.

Referring still to FIG. 1, once the planning phase has been completed, e.g., the area of interest has been identified and the pathway thereto selected, and registration has been completed, system 10 may be utilized to navigate LG 92 through the patient's airway to the area of interest. To facilitate such navigation, computer 80, monitoring equipment 60, and/or any other suitable display may be configured to display the three-dimensional model including the selected pathway from the current location of sensor 94 of LG 92 to the area of interest. Navigation of LG 92 to the area of interest using tracking system 70 is similar to that detailed above and, thus, is not detailed herein for the purposes of brevity.

Once LG 92 has been successfully navigated to the area of interest, completing the navigation phase, LG 92 may be unlocked from EWC 96 and removed, leaving EWC 96 in place as a guide channel for guiding tools 100a, 100b, 100c to the area of interest. Alternatively, tools 100a, 100b, 100c may be utilized in lieu of LG 92 using sensor 100d, as noted above. For a detailed description of exemplary navigation and planning phases, reference may be made to U.S. patent application Ser. No. 14/753,288 to Brown et al., previously incorporated by reference.

The electromagnetic waves generated by transmitter mat 76 are received by the various sensor elements of the sensor assembly of the tools 100a, 100b, 100c or sensor 94 of LG 92, and are converted into electrical signals that are sensed via reference sensors 74. Tracking system 70 further includes reception circuitry (not shown) that has appropriate amplifiers and A/D converters that are utilized to receive the electrical signals from reference sensors 74 and process these signals to determine and record location data of the sensor assembly. Computer 80 may be configured to receive the location data from tracking system 70 and display the current location of the sensor assembly on the three-dimensional model and relative to the selected pathway generated during the planning phase, e.g., on computer 80, monitoring equipment 60, or other suitable display. Thus, navigation of tools 100a, 100b, 100c and/or LG 92 to the target tissue and/or manipulation of tools 100a, 100b, 100c relative to the target tissue, as detailed above, can be readily achieved.

It is contemplated that the above described procedure may be alternatively performed using a laparoscopic or open approach. In this manner, the clinician may apply a clip, clamp, or other similar device (not shown) on the airway in fluid communication with the portion of the lungs including the area of interest. Similarly to that described above, the clinician records and enters the clinical effects of isolating the portion of the lungs including the area of interest in the database for future use.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A system comprising:
   a memory storing one or more images of a patient and one or more software applications;
   a display configured to present the one or more images of a patient;
   a user interface adapted to be presented on the display in combination with the one or more images of a patient enabling the identification of one or more image locations illustrating the effects of chronic obstructive pulmonary disease (COPD);
   an extended working channel navigable to one or more actual locations within a patient corresponding to the one or more image locations;
   an electromagnetic field generator;
   a first sensor associated with the extended working channel, the first sensor detecting a field produced by the electromagnetic field generator, wherein the sensed field enables determination of the location of the first sensor in the electromagnetic field;
   a processor, executing one of the one or more software applications to register the one or more images of a patient with the determined location of the first sensor such that the determined location of the first sensor is presented on the user interface; and
   a catheter, extendible through the extended working channel, the catheter configured to temporarily isolate a portion of a patient's lungs including the one or more actual locations by evacuating air from within the portion of the lungs including the one or more actual locations,
   wherein the processor, executing one of the one or more software applications, is configured to predict a clinical consequence of evacuating air from within the portion of the lungs including the one or more actual locations.

2. The system of claim 1, further including an endobronchial valve, the endobronchial valve deployable by the catheter to temporarily induce atelectasis of the portion of a patient's lungs including the one or more actual locations within a patient corresponding to the one or more image locations illustrating the effects of COPD.

3. The system of claim 1, further including a distal balloon, the distal balloon disposed on a distal portion of the catheter and expandable to facilitate temporarily sealing the portion of a patient's lungs including the one or more actual locations within a patient corresponding to the one or more image locations illustrating the effects of COPD.

4. The system of claim 3, wherein the catheter includes a lumen defined therethrough such that air may be evacuated from the sealed portion of a patient's lungs to temporarily induce atelectasis.

5. The system of claim 3, wherein the catheter includes a lumen defined therethrough such that fluid is injected through the lumen and into the sealed portion of a patient's lungs to evacuate air from the sealed portion of a patient's lungs to temporarily induce pulmonary consolidation.

6. The system of claim 1, wherein the catheter includes a tapered distal tip, the tapered distal tip capable of being wedged within an airway of a patient's lungs to temporarily seal the portion of a patient's lungs including the one or more actual locations within a patient corresponding to the one or more image locations illustrating the effects of COPD.

7. The system of claim 5, wherein the lumen of the catheter is configured such that air may be evacuated from the sealed portion of a patient's lungs to temporarily induce atelectasis.

8. The system of claim 5, wherein the lumen of the catheter is configured such that a fluid may be injected through the lumen of the catheter and into the sealed portion of a patient's lungs to evacuate air from the sealed portion of a patient's lungs to temporarily induce pulmonary consolidation.

9. The system of claim 1, wherein evacuating air from within a portion of a patient's lungs including the one or more actual locations within a patient corresponding to the one or more image locations illustrating the effects of COPD temporarily induces atelectasis.

10. The system off claim 1, wherein evacuating air from within a portion of a patient's lungs including the one or more actual locations within a patient corresponding to the one or more image locations illustrating the effects of COPD temporarily induces pulmonary consolidation.

11. A system, comprising:
    a memory storing one or more images of a patient and a software application;
    a display configured to present the one or more images of the patient;
    a user interface adapted to be presented on the display in combination with the one or more images of the patient enabling the identification of one or more image locations illustrating the effects of chronic obstructive pulmonary disease (COPD);
    an extended working channel navigable to one or more actual locations within the patient corresponding to the one or more image locations;
    a catheter, extendible through the extended working channel, the catheter configured to temporarily isolate a portion of the patient's lungs including the one or more actual locations by evacuating air from within the portion of the patient's lungs including the one or more actual locations; and
    a processor, executing the software application, configured to predict a clinical consequence of evacuating air from within the portion of the lungs including the one or more actual locations.

12. The system of claim 11, further comprising an endobronchial valve deployable by the catheter to temporarily induce atelectasis of the portion of the patient's lungs including the one or more actual locations.

13. The system of claim 11, further comprising a distal balloon disposed on a distal portion of the catheter and configured to expand to temporarily seal the portion of the patient's lungs including the one or more actual locations.

14. The system of claim 13, wherein the catheter includes a lumen defined therethrough such that air may be evacuated from the temporarily sealed portion of the patient's lungs via the lumen to temporarily induce atelectasis.

15. The system of claim 13, wherein the catheter includes a lumen defined therethrough configured to facilitate delivery of a fluid into the temporarily sealed portion of the patient's lungs to evacuate air from the temporarily sealed portion of the patient's lungs to temporarily induce pulmonary consolidation.

16. A system comprising:
    a memory storing one or more images of a patient and a software application;

a display configured to present the one or more images of the patient;

a user interface adapted to be presented on the display in combination with the one or more images of the patient enabling the identification of one or more image locations illustrating the effects of chronic obstructive pulmonary disease (COPD);

an extended working channel navigable to one or more actual locations within the patient corresponding to the one or more image locations;

an electromagnetic field generator;

a processor, executing the software application to register the one or more images of the patient with a location of the extended working channel such that the location of the extended working channel is presented on the user interface; and a catheter, extendible through the extended working channel, the catheter configured to temporarily isolate a portion of the patient's lungs including the one or more actual locations by evacuating air from within the portion of the lungs including the one or more actual locations, wherein the processor, executing the software application, is configured to predict a clinical consequence of evacuating air from within the portion of the patient's lungs including the one or more actual locations.

17. The system of claim 16, further comprising an endobronchial valve deployable by the catheter to temporarily induce atelectasis of the portion of the patient's lungs including the one or more actual locations.

18. The system of claim 16, further comprising a distal balloon disposed on a distal portion of the catheter and configured to expand to temporarily seal the portion of the patient's lungs including the one or more actual locations.

19. The system of claim 18, wherein the catheter includes a lumen defined therethrough such that air may be evacuated from the temporarily sealed portion of the patient's lungs via the lumen to temporarily induce atelectasis.

20. The system of claim 18, wherein the catheter includes a lumen defined therethrough configured to facilitate delivery of a fluid into the temporarily sealed portion of the patient's lungs to evacuate air from the temporarily sealed portion of the patient's lungs to temporarily induce pulmonary consolidation.

* * * * *